US006607597B2

(12) United States Patent
Sun et al.

(10) Patent No.: US 6,607,597 B2
(45) Date of Patent: Aug. 19, 2003

(54) METHOD AND APPARATUS FOR DEPOSITION OF PARTICLES ON SURFACES

(75) Inventors: James J. Sun, New Brighton, MN (US); Benjamin Y. H. Liu, North Oaks, MN (US)

(73) Assignee: MSP Corporation, Shoreview, MN (US)

( * ) Notice: Subject to any disclaimer, the term of this patent is extended or adjusted under 35 U.S.C. 154(b) by 101 days.

(21) Appl. No.: 09/772,688

(22) Filed: Jan. 30, 2001

(65) Prior Publication Data
US 2002/0100416 A1 Aug. 1, 2002

(51) Int. Cl.[7] ................................ B05C 19/00
(52) U.S. Cl. ................................ 118/309; 118/308
(58) Field of Search ................................ 118/308, 309, 118/326, 319, 320, 52, 612, 715; 427/240, 585, 99

(56) References Cited

U.S. PATENT DOCUMENTS

| | | | | | |
|---|---|---|---|---|---|
| 4,284,495 | A | | 8/1981 | Newton | 209/3.1 |
| 4,301,002 | A | | 11/1981 | Loo | 209/143 |
| 4,610,760 | A | * | 9/1986 | Kirkpatrick et al. | 159/4.01 |
| 4,670,135 | A | | 6/1987 | Marple et al. | 509/143 |
| 4,761,074 | A | * | 8/1988 | Kohsaka et al. | 365/37 |
| 4,767,524 | A | | 8/1988 | Yeh et al. | 209/143 |
| 4,788,082 | A | | 11/1988 | Schmitt | 427/248.1 |
| 4,794,086 | A | * | 12/1988 | Kasper et al. | 436/36 |
| 4,886,359 | A | | 12/1989 | Berndt | 356/312 |
| 4,990,740 | A | | 2/1991 | Meyer | 219/121.52 |
| 4,996,080 | A | | 2/1991 | Daraktchiev | 427/57 |
| 5,150,036 | A | | 9/1992 | Pourprix | 324/71.4 |
| 5,171,360 | A | | 12/1992 | Orme et al. | 75/331 |
| 5,203,547 | A | * | 4/1993 | Marumo | 269/21 |
| 5,229,171 | A | | 7/1993 | Donovan et al. | 427/483 |
| 5,306,345 | A | | 4/1994 | Pellet et al. | 118/301 |
| 5,316,579 | A | | 5/1994 | McMillan et al. | 118/50 |
| 5,364,562 | A | | 11/1994 | Wang | 423/593 |
| 5,456,945 | A | | 10/1995 | McMillan et al. | 427/252 |
| 5,534,309 | A | | 7/1996 | Liu | 427/458 |
| 5,540,772 | A | | 7/1996 | McMillan et al. | 118/50 |
| 5,614,252 | A | | 3/1997 | McMillan et al. | 427/99 |
| 5,688,565 | A | | 11/1997 | McMillan et al. | 427/565 |
| 5,807,435 | A | | 9/1998 | Poliniak et al. | 118/504 |
| 5,916,640 | A | | 6/1999 | Liu et al. | 427/475 |
| 5,962,085 | A | * | 10/1999 | Hayashi et al. | 427/585 |

FOREIGN PATENT DOCUMENTS

WO WO 98/09731 3/1998

OTHER PUBLICATIONS

H.H. Zhong et al., "Deposition of superconductive YbaCuO films at atmospheric pressure by RF plasma aerosol technique", AIP Conf. Pro. (219) 1, pp. 531–542.

Q.H. Powell et al., "Gas–phase coating of TiO2 with SiO2 in a continuous flow hot wall aerosol reactor", J.Mat.Res. (12), 2, pp. 552–559.

V. Moshnyaga, "Preparation of rare–earth manganite–oxide thin films by metalorganic aerosol deposition technique", App. Phys. Lett. (74) 19, pp.2842–2844.

* cited by examiner

*Primary Examiner*—Richard Crispino
*Assistant Examiner*—Yewebdar T Tadesse
(74) *Attorney, Agent, or Firm*—Westman, Champlin & Kelly, P.A.

(57) ABSTRACT

A deposition system is used for depositing particles onto a substrate, such as a wafer in a deposition chamber. The particles are carried in an aerosol that is generated by an atomizer that includes an impaction plate for removing large particles before the aerosol is discharged, and which has an output that is provided through a particle classifier to the deposition chamber. Various branches of flow lines are used such that the aerosol that has classified particles in it, is mixed with a clean dry gas prior to discharge into the deposition chamber, and selectively the aerosol can be directed to the deposition chamber without having the particles classified. The lines carrying the aerosol can be initially connected to a vacuum source that will quickly draw the aerosol closely adjacent to the deposition chamber to avoid delays between deposition cycles.

21 Claims, 4 Drawing Sheets

FIG. 2

FIG. 3

METHOD AND APPARATUS FOR DEPOSITION OF PARTICLES ON SURFACES

BACKGROUND OF THE INVENTION

Figure 1:
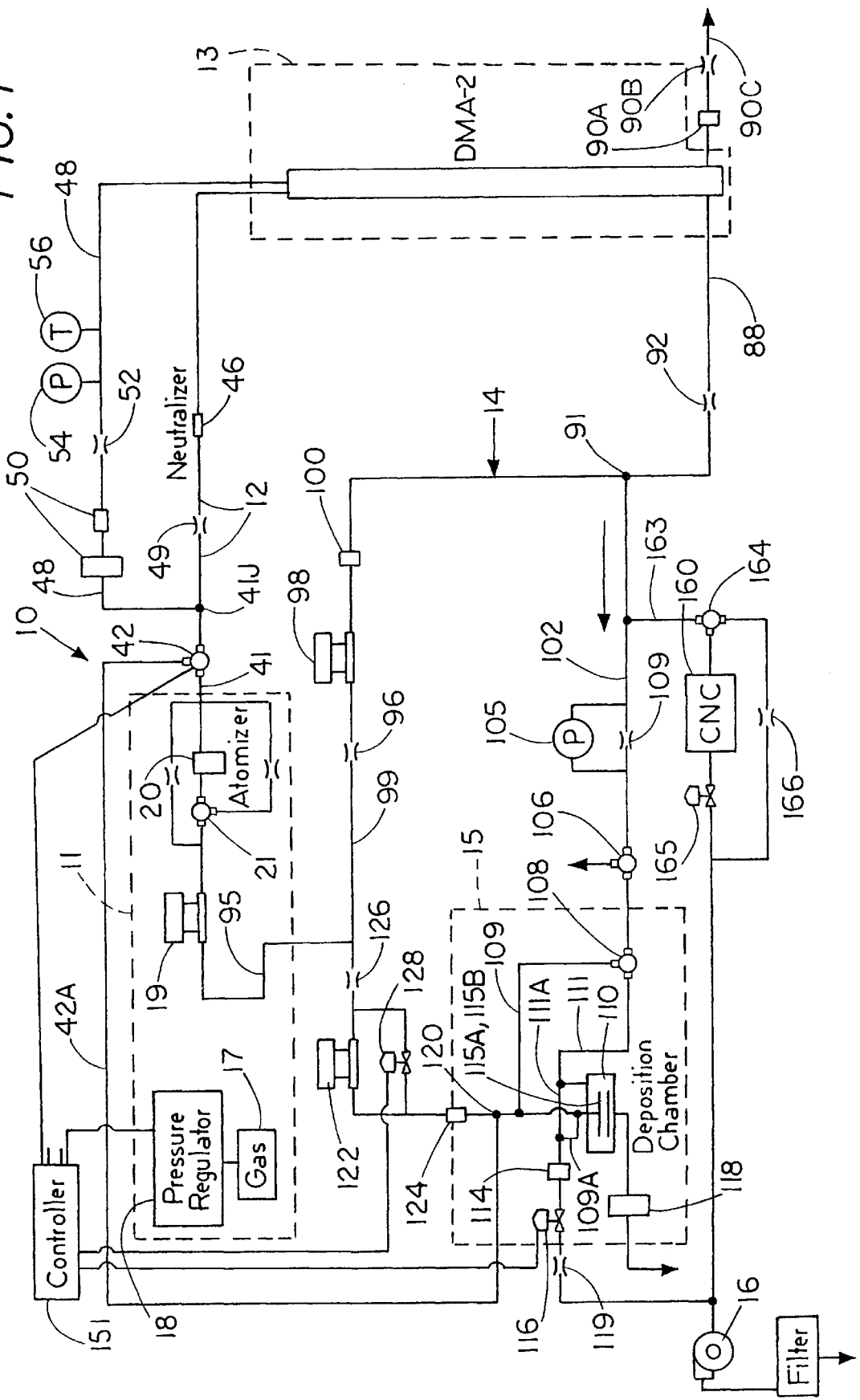

The present invention relates to a method and apparatus for deposition of particles on surfaces, wherein the particles are provided from an aerosol generation device that regulates the droplet size and concentration provided to the deposition chamber so that precisely sized particles or spheres are deposited on the surface.

Pneumatic atomizers are often used for generating aerosols containing polystyrene latex (PSL) spheres or particles, as well as other particles, For subsequent deposition on substrates, such as semiconductor wafers. The particles are first suspended in liquid such as deionized water to form a suspension. The suspension is then atomized to form droplets. When the droplets evaporate, the PSL spheres or particles become airborne particles. The generation rate of PSL spheres or particles is a function of droplet generation rate of the atomizer and the probability for a droplet to contain PSL spheres or particles.

The droplets produced by a pneumatic atomizer normally have a broad size distribution ranging from less than 0.1 $\mu$m to larger than 10 $\mu$m. Large droplets have a high probability to contain more than one PSL sphere or particle. If a droplet contains more than one PSL sphere or particle, it is called a multiplet. Multiplets provide more PSL particles than those wanted.

A droplet that does not contain any particles is called an empty droplet. When an empty droplet evaporates, it forms a residue particle resulted from the precipitation of nonvolatile impurities dissolved in the atomizing solution. For example, to prepare a PSL suspension, surfactant is often used to keep suspended PSL spheres from coagulating. The surfactant is one of the sources for residue particles. The size of residue particles depends on the size of the droplets and the concentration of nonvolatile impurities in the atomizing solution. At a given concentration of the nonvolatile impurity, the residue particle size is linearly proportional to the droplet size.

For PSL or particle deposition, the multiplets and the residue particles are always unwanted. Special atomizers will minimize the formation of multiplets and the size of residue particles by removing large size droplets.

SUMMARY OF THE INVENTION

The present invention relates to a system for depositing particles on surfaces, in particular semiconductor wafers. The invention insures that there is a minimal amount of unwanted material deposited on the wafer, and that each droplet of the aerosol contains only one sphere or particle. Residues are minimized, and the deposit is uniformly made.

The present invention, in one aspect, provides for an atomizer that will atomize droplets that are only within a particular size range, and will insure that the droplets from the atomizer are of size so they will contain only one particle of the desired material that is going to be deposited. In this way, empty droplets are avoided, and multiplets, that is, a droplet that contains more than one particle, are also avoided.

A differential mobility analyzer, which can be adjusted to emit only the particles that are of proper size, is utilized for insuring one size particle.

Various forms of devices are included for checking the density of the particles in the aerosol and the flow rate. The flow lines permit adding clean gas to the flow of the aerosol as needed, and a pre-deposition sequence permits the aerosol flow to be established at a junction adjacent to the deposition chamber and then switched to the deposition chamber. The procedure reduces the time between deposition cycles.

BRIEF DESCRIPTION OF THE DRAWINGS

FIG. 1 is a schematic representation of a wafer deposition system made according to the present invention;

FIG. 2 is a flow diagram illustrating the control of the gas that is used in the atomization process;

FIG. 3 is a schematic sectional view of a atomizer arrangement used with the present invention;

FIG. 4 is a vertical sectional view of a differential mobility analyzer used in the present invention;

FIG. 5 is a schematic diagram showing two differential mobility analyzers used to broaden the size range of particles that can be processed;

FIG. 6 is a schematic diagram of the aerosol flow lines adjacent the deposition chamber; and FIG. 7 is a schematic representation of connections of a particle counter.

DETAILED DESCRIPTION OF THE PREFERRED EMBODIMENTS

Referring to FIG. 1, a schematic diagram of an entire wafer deposition system is illustrated generally at 10, and includes an aerosol generator or atomizer section 11, which will provide an aerosol along a line 12 to a differential mobility analyzer 13, that classifies the aerosol particles according to size and passes the classified particles along a line system 14 to a deposition chamber illustrated generally at 15. Chamber 15 is used for depositing particles carried in the aerosol onto a wafer. Deposition chambers are well known in the art. A fluid flow through the lines is provided by the positive pressure at the aerosol generator and by a vacuum pump. Vacuum pump 16 is not used to evacuate the deposition chamber, but is used to establish initial flow in the lines and through a particle counter.

The individual sections have valves, flow controllers, pressure regulators, and the like as will be explained in connection with the individual sections.

FIG. 2 illustrates the atomizer section 11. A source of clean dry gas 17 provides the gas through a pressure regulator 18, a mass flow controller 19, and a three way valve 21 to an atomizer indicated generally at 20. The mass flow controller 19 controls the mass flow from the pressure regulator 18 to the atomizer 20 The flows are balanced and clean gas can be added to and mixed with the atomizer output.

As shown in FIG. 3, atomizer 20 has a body 23 with an air or gas inlet passageway 23A from the flow controller 18. The flow passes through an orifice 23D into an atomization chamber or nozzle 23B into which an atomizing liquid 23L from a container is drawn. The liquid is broken up into droplets in chamber or nozzle 23B. An impaction plate 22 is installed adjacent to but spaced from the outlet of the atomizer nozzle 23B to remove large droplets by impaction. The impaction plate 22 can be an annular band or wall, if desired.

Three parameters for determining the output droplet size and volume are dimensions of the orifice or passageway 23D between inlet passageway 23A and atomizer nozzle 23B, the diameter of the nozzle 23B, and the distance from the outlet opening of nozzle 23B and the impaction plate 22. The diameter of orifice 23D is identified as D1 and indicated by arrows 24, the diameter of the output nozzle 23B is identified as D2 and indicated by arrows 26. The distance from the nozzle 23B outlet to the impaction plate surface is identified as D3 and indicated by arrows 28. Atomizing orifice 23D controls the total atomizing gas flow. When D1 is constant, reducing dimension D2, the outlet diameter of the nozzle 23B, and reducing dimension D3, the distance from the nozzle outlet to the impaction plate surface, will result in a smaller output droplet size. By selectively changing D2 and D3, the size of the droplets produced by the atomizer can be regulated. The droplet size is selected so each droplet will contain one PSL particle. The PSL particles are also regulated in size, and the goal of no empty droplets and no multiplets can be achieved. With different types of particles, this goal also can be achieved by appropriate sizing of the orifice 23D, the atomizing nozzle 23B, and the distance from the nozzle to the impaction plate.

Figures 2, 3:
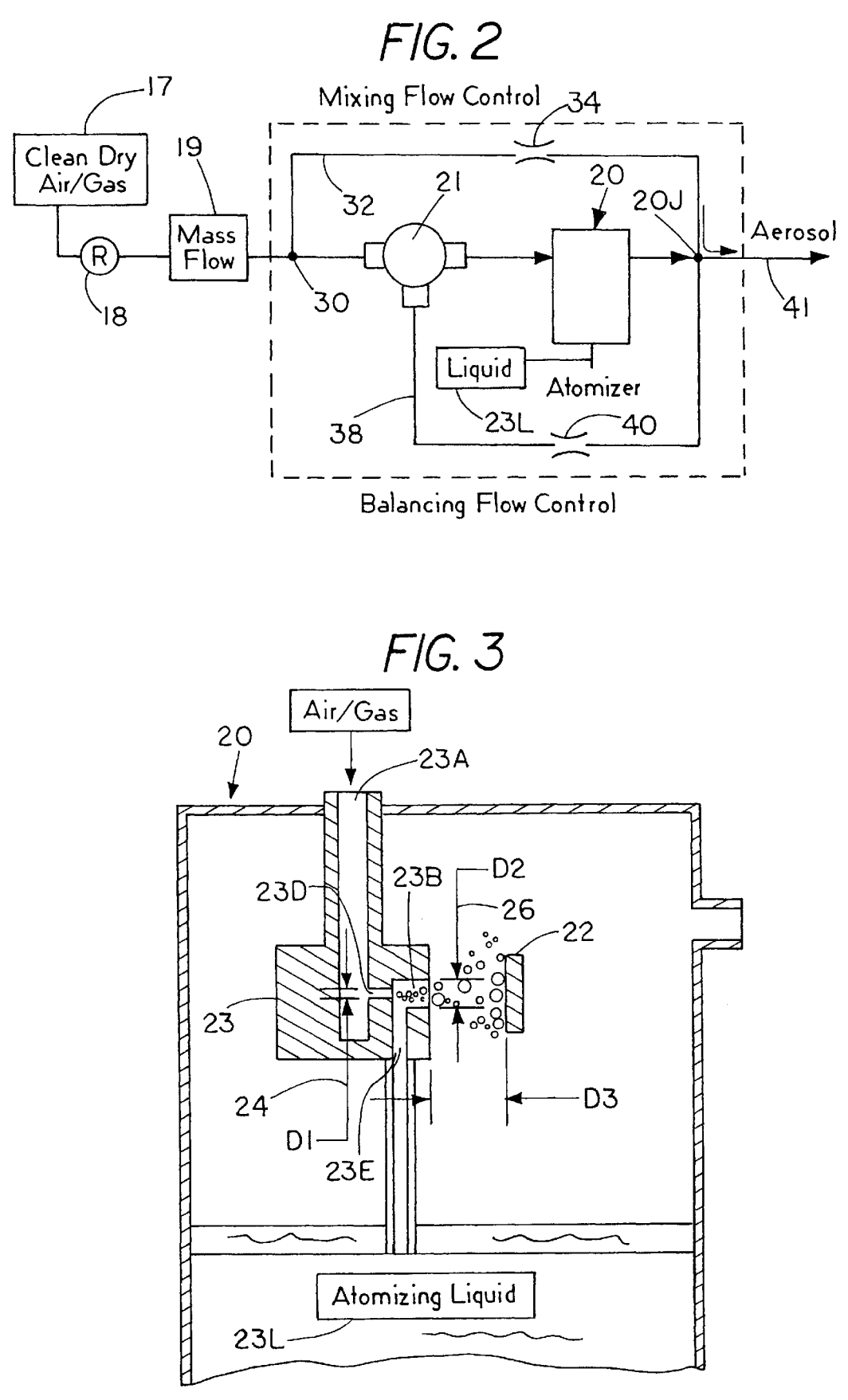

The aerosol produced from the atomizer 20 of FIG. 3, and other atomizers, consists of droplets carried in a saturated gas, usually air. One way to evaporate the droplets is to mix the aerosol droplets with dry gas or air. Referring to FIG. 2, the clean dry gas from source 17 and mass flow controller 19 splits into two streams at a junction 30. The atomizing gas flows into the 3-way valve 21. A mixing gas flow is diverted from a junction 30 along a line 32, through a mixing flow control comprising an orifice 34 One port of the 3-way valve 21 is selectively connected to the inlet of atomizer 20 and the other port of valve 27 is selectively connected to a bypass line 38 which has balancing flow control orifice 40. The output lines from the atomizer, line 32, and line 38 join at junction 20J.

During aerosol generation, the 3-way valve 21 is connected to the inlet passage 23A of the atomizer 20, producing aerosol droplets. The aerosol droplets then mix with a controlled volume of clean dry air/gas from the mixing flow control orifice 34. If the atomizer 20 is to be shut off, the valve 21 directs flow through balancing flow control orifice 40.

The flow from 3-way valve 21 through the inlet passage 23A, orifice 23D and nozzle 23B of the atomizer 20 produces the aerosol droplets by aspirating liquid containing PSL particles (or other particles) from the liquid and particle source 23L. The aerosol droplets then mix with clean dry air or other gas provided at a junction 20J from the mixing flow control. After mixing, the droplets will evaporate, forming an aerosol of PSL spheres or particles for deposition. One way to control the three flows, that is, the aerosol flow, the mixing flow and balancing flow is using properly sized orifices. The control orifice 34 for the mixing flow, the orifice 23D for the atomizing flow and the orifice 40 for the balancing flow are sized such that at a given pressure of the clean dry gas or air, the total flow through the aerosol generator to line 41 is a constant regardless of whether the 3-way valve 21 provides the input flow to the atomizer for atomizing liquid or to the balancing flow control orifice. The atomizing flow is shut off when the valve 21 is moved to provide flow to the line 38.

The output from the atomizer in line 41, goes through a 3-way valve 42. The valve 42 can divert the aerosol along a line 42A that bypasses the size classification. The normal operating position of valve 42 will transmit the aerosol to a junction 41J (see FIG. 1) in the line 12 where the desired flow goes to the differential mobility analyzer 13.

The line 12 has a flow control orifice 44 in the line, as well as a charge neutralizer 46, which will de-ionize the aerosol, and reduce electrical charges from the particles. The line 12 is branched at junction 41J to line 48, that passes through a filter 50, and a flow control restriction 52. The flow control restriction 52 is illustrated as an orifice, but also could be a mass flow controller. The flow restriction will control the volume of the aerosol that is diverted through the line 48 and through filter 50 as a function of the total flow and the flow provided to the DMA 13. A pressure sensor 54 is used for sensing the pressure in the line 48, and keeping it regulated appropriately, and a temperature sensor 56 is also utilized. These parameters are utilized as feedback for controlling the inputs to the DMA. The line 48 is connected to the sheath flow input to the differential mobility analyzer, and provides what is called the DMA sheath flow. The filter 50 removes most of the particles in the aerosol, so the sheath flow is essentially a clean gas.

The aerosol in the line 12 is injected into the center of the DMA. The DMA will discharge only particles that are of a desired size. The DMA is used to insure that the particles that are to be provided to the deposition chamber will be only one size or monodisperse.

Figure 4:
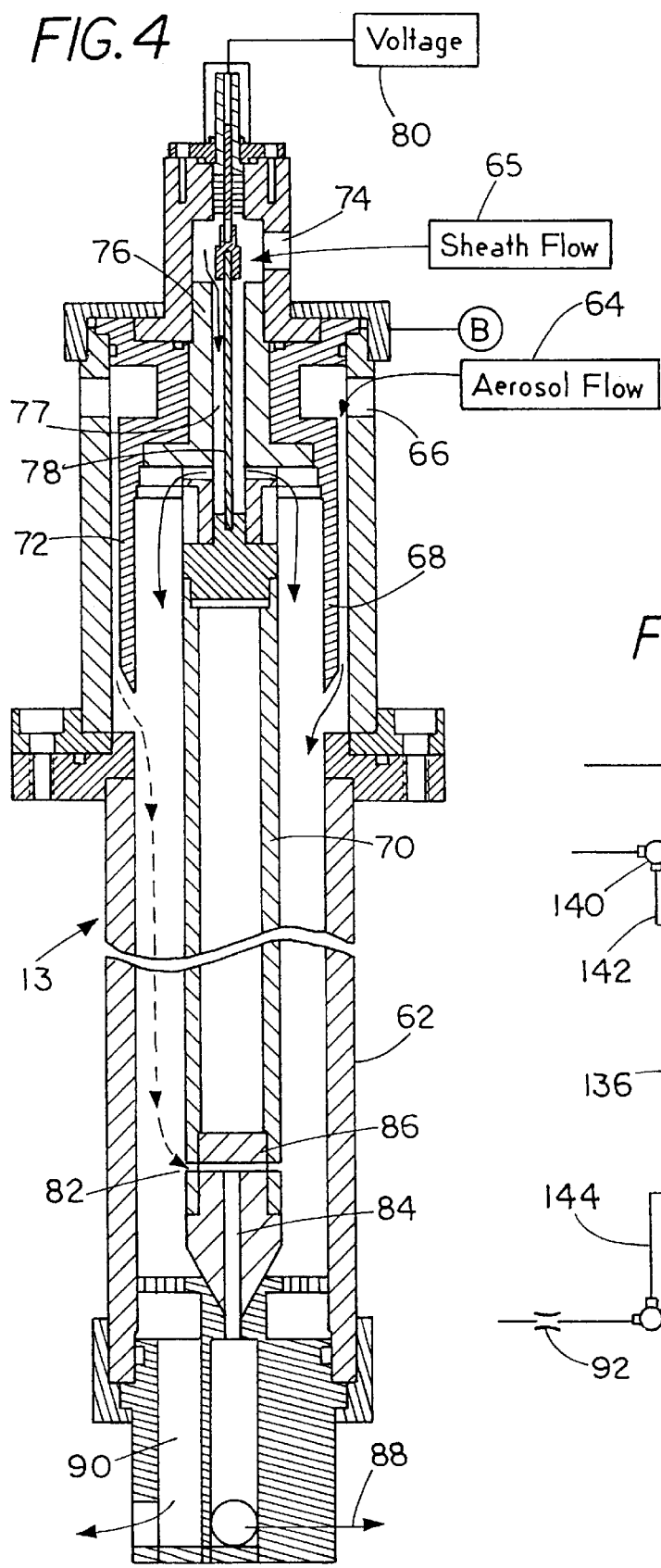

The differential mobility analyzer (DMA) 13 is shown in detail in FIG. 4, and it operates to classify particles so that they are monodisperse particles. The DMA 13 comprises a tubular housing 62 through which the divided flow from the atomizer 20 passes and includes the sheath flow from line 48 as mentioned, as well as the aerosol flow from line 12. The aerosol flow, which is indicated by the block 64 in FIG. 4 enters ports 66 in the housing 62 and flows down through an annular passageway 68 formed between the inner surface of housing 62 and a flow distributor 72, which is a sleeve spaced from the outer housing to provide an aerosol flow passageway, and surrounds a central electrode 70, which is a tubular electrode. The aerosol flow thus surrounds and is spaced from the tubular central electrode 70. The aerosol flows down along the outside of the flow distributor sleeve 72, so that it stays along the inside surface of the housing 62. The sheath flow, indicated by block 65, from line 12 is introduced through a port 74, and flows down through a central passageway 77 of an insulator sleeve 76 that has a high voltage electrode 78 which is connected to a source of high voltage and which extends through the central passageway, and connects to the tubular high voltage electrode 70.

As the sheath flows down through the passageway 77, it will be discharged into the interior of the flow distributor 72 and flow down along the surfaces of the tubular electrode 70 to provide a sheath of clean air surrounding the electrode. The aerosol particles carrying a low level of electrical charge, as they move from the inlet end 66 of the DMA housing 62 to the outlet, the voltage on the electrode 70 is set so the correct size of particles will be attracted to enter an opening shown at 82 in the side wall of the electrode, and then discharge out through a central passageway 84 in an end piece 86 of the tubular electrode 70. The particles of the selected size discharge out through a line 88. The output of the DMA is a monodispersed aerosol, that is, an aerosol with only one size particle. The voltage from the source 80 controls the size of the particles that will enter the opening 82, and at a set voltage only one size will pass through the passageway 84 and the line 88.

Excess flow and containing particles that are of a different size from that which will pass through the opening 82, are carried out through an excess flow passageway 90, and through a filter 90A, a flow controller 90B and a line 90C to a desired location.

The total flow from the aerosol generator 11 can be maintained at a set level, the flow from one outlet of valve 42 is split into two flow streams, one for the DMA sheath flow and the other comprising a polydisperse aerosol flow to be size-classified by the DMA. The ratio of the DMA sheath flow rate to polydisperse aerosol flow rate is controlled by the two flow restrictions 44 and 52 shown in FIG. 1. All the particles in the DMA sheath flow are removed by filter 50 (which can have two sections) prior to the flow restriction or flow control device 52. The flow restriction or flow control device 52 for the sheath flow can be an orifice flow restriction or a flow controller such as a mass flow controller. The polydisperse aerosol flow in line 12 cannot be satisfactorily controlled by a mass flow controller since the flow carries a high concentration of particles, some of which would be removed by a mass flow controller.

The flow restriction device 34 is an orifice or similar device that will restrict the aerosol flow without loss of particles. The ratio of the DMA sheath flow rate to the polydisperse aerosol flow rate is fixed if orifices are used for controlling both DMA sheath flow and the polydisperse flow. The ratio can be adjusted by adjusting the sheath flow rate with flow control device 52 if it is a flow controller. The total flow through the DMA is kept constant, and the output particle size is controlled by the voltage of source 80.

The DMA monodisperse aerosol output flow from DMA 13 that is directed to line 14 is controlled by orifice 92. The DMA excess flow can be controlled by an orifice 90B or a flow controller. When using an orifice to control both flows from the DMA, the two orifices are properly sized to keep a constant ratio of the flow rates in lines 88 and 90C. When the DMA excess flow in line in 90C is controlled by a flow controller, the ratio of the two flow rates, that is the ratio of flows in lines 88 and 90C, can be adjusted by adjusting the DMA excess flow with a flow controller replacing orifice 90B.

Figure 5:
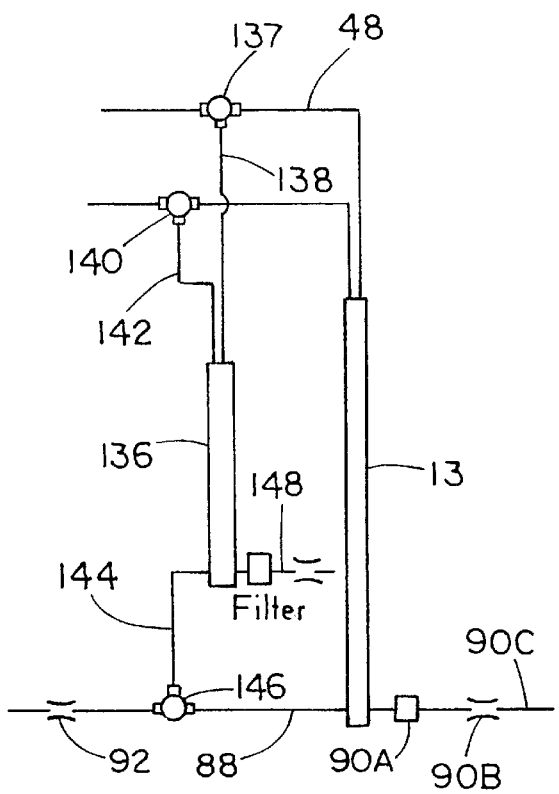

As shown in FIG. 5 two differential mobility analyzers are provided in a modified embodiment of the invention to widen the size range of particles that can be provided in the monodisperse flow to the deposition chamber. DMA 13 has a long housing and flow path and can classify particles in a size range from 0.10 to 2.0 μm. An additional short housing DMA 136 will classify a range of particles from 0.01 to 0.3 μm. The DMA 136 operates in the same manner as DMA 13, except the parts are made to suit the smaller size particles. When combined, the Dual-DMA system covers a size range from 0.01 to 2.0 μm.

To accommodate two DMA's, a 3-way valve 137 is placed in line 48 downstream from flow restriction 52. A line 138 is connected to one output of valve 137 and carries the sheath flow to DMA 136 when valve 137 is in position to connect line 48 to line 138. The polydisperse aerosol line 12 is branched with a 3-way valve 140 and a connected line 142 to the aerosol input of the DMA 136. The DMA 136 is constructed as shown for the DMA 13, but the different length and other known design dimensions results in being operable for the different range of particle sizes.

The monodisperse outlet line 144 of DMA 136 is connected through a 3-way valve 146 to the output line 88 of DMA 13, upstream from the flow restriction 92. The excess flow from DMA 136 is discharged through a filter 147 and line 148. The excess flow can be discharged as desired. The 3-way valves 137, 140 and 146 can be simultaneously operated by a central controller 151 when the output from atomizer 11 is providing particles in the range for the respective DMA. The controller 151 is used to control all the valve flow controllers, pressure regulators and the like. Feedback from the pressure sensors, temperature sensors and flow sensor are used by central controller 151 to provide the proper adjustments.

As shown in FIG. 1, after the monodisperse flow passes through flow restrictor or flow control orifice 92, the monodispersed aerosol flow can be mixed at a junction 91 with a clean gas or air, that is fed from a junction 97 on the output line 18A of regulator 18 through branch line 94 and 95. Line 94 has an orifice 96, a flow controller 98 and a filter 100 for regulating flow and for removing any particles. The particle carrying gas, mixed with the dry clean gas to achieve the correct particle density in the flow moves along a line 102. A further flow control restrictor 104 is provided. A first 3-way valve is provided to selectively direct the flow to a waste line when deposition is not desired.

A second 3-way valve 108 in line 102 is used to direct the aerosol flow either to a spot deposition nozzle in a deposition chamber 110 along line 111 or to a deposition showerhead along a line 109. The deposition chamber 110 can be made as desired. The aerosol is then deposited onto a wafer in the chamber with the exhaust going through a filter 118. The flow through the deposition chamber 110 is determined by pressure differentials in the lines used.

If desired, the flow from the output of the valve 108 along lines 111 and 109 can be drawn directly to the vacuum pump 16 through a filter 114, and an on/off valve 116. When valve 116 is open, flow will pass through a flow restrictor 119 and then to the low pressure side of the vacuum pump 16. Additional filters can be provided as desired. The line 109 from the 3-way valve 108 is coupled into a line 120 which, as shown, is also connected to the output of a pressure regulator 18 through line 95, a flow restrictor 126, a flow controller 122, and a filter 124. An on/off valve 128 provides a bypass around the flow controller 122. Flow restrictor 126 remains in the flow lines regardless of whether valve 128 is on or off.

The flow from line 95 also can be sent through flow controller 122 as a purge flow to purge the deposition chamber with clean dry air or gas.

If desired, the output aerosol from the atomizer 20 can be diverted by valve 42 along the line 42A to line 120 and thus to the deposition chamber for direct deposition, without passing the aerosol through the DMA. The direct deposition function is normally used for depositing large size PSL particles (500–4000 nm). In this case, the residue particles are not of concern since they are normally much smaller. Typically, residue particles are smaller than 30 to 50 nm under normal operating conditions of atomizers presently available.

Figure 6:
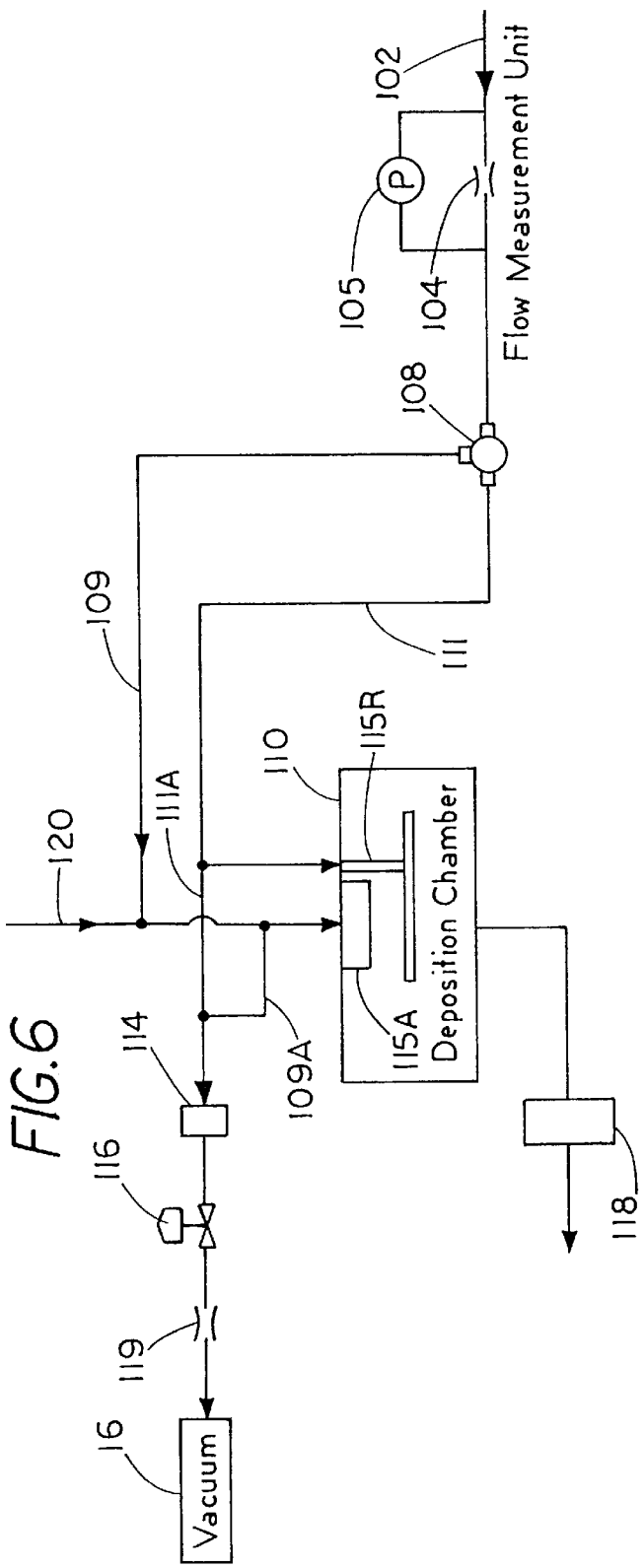

Another feature of the present invention is shown in FIG. 6. The response time for the deposition system 10 can be reduced by reducing the time lag for introducing the aerosol from lines or passages 111 or 109 to deposition chamber 110. Prior to deposition, the aerosol is drawn to the close vicinity of the deposition chamber 110 by vacuum from vacuum pump 16 as controlled by on/off valve 116. The vacuum pump 16 is designed such that it will provide a flow that is slightly higher than the required deposition aerosol flow. When the valve 116 is turned on (open), the aerosol from any one of the lines 109, 111, or 120 will be pulled from valve 108 and line 109 or line 111 to the exhaust by the vacuum pump 16. In addition, since the vacuum flow rate is slightly higher than the desired deposition aerosol flow, there will be a small reverse flow from the deposition chamber 110, via the deposition nozzle 115B or the deposition showerhead 115A (see FIG. 6), to the vacuum pump 16 when the valve 116 is turned on. This flow will remove contaminates from the deposition chamber and will cause the respective line 109 or 111 (depending on the setting of valve 108) or from line 120 if it is being used, to fill with the aerosol down to the junction with lines 109A and 111A, connecting the main portions of these lines to valve 116.

The spot deposition nozzle 115B is connected to line 111 and is for depositing particles in controlled size spots on a wafer. The deposition showerhead 115A is connected to line 109 and is for larger area deposition, as is well known.

After valve 116 has been on sufficiently so the line 109 or 111 is filled with the desired aerosol and the deposition chamber 110 is purged by the reverse flow, the on/off valve 116 will be shut off and the aerosol in either line 109 or line 111 will enter the deposition chamber immediately because of the close coupling of the lines to the chamber and the prefilling of the lines with the correct aerosol. The deposition response time is thus significantly improved by providing the preflow out the vacuum pump 16.

After each deposition cycle, the valve 116 for the vacuum control is turned on by central controller 151. The residual particles in the spot deposition nozzle or in the deposition showerhead after each deposition will, therefore, be sucked to the vacuum source. Cross contamination of particles between depositions is avoided.

Also as shown in FIGS. 1 and 6, orifice 104 is used for flow measurement in combination with a differential pressure sensor 105 to measure and monitor the deposition flow of mono size aerosol flow in line 102. During deposition, the deposition flow and aerosol concentration are continuously monitored and the deposition time is dynamically adjusted, based on the measured aerosol concentration and deposition flow rates.

A particle counter 160 (FIGS. 1 and 7) which is a condensation nuclei counter (CNC) is used to determine aerosol concentration by counting the number of particles that pass through the counter when the flow is held at a standard flow rate. The counter input line 162 is connected to line 102 through line 163 and a valve 164. The particle concentration can be measured at set intervals or for a set time as each deposition cycle starts. The output line from the counter 160 is connected to vacuum pump 16.

Figure 7:
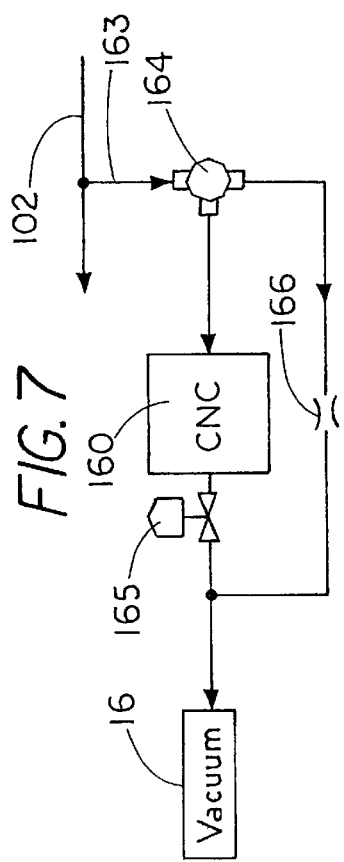

As shown in FIG. 7, a flow restriction device or orifice 166 in a bypass line is used to control the CNC bypass flow. The flow restriction device 166 is sized to have the same flow rate as the CNC 160 sampling flow rate. That is, the flow rate through the line 163, which carries flow from line 102 to the CNC counter 160 or, when the counter is shut off, to flow restriction 166, is kept as a constant, whether the valve 164 is turned to provide flow to the CNC 160 or turned to provide flow through the flow restriction 166. The constant bypass flow through the CNC or restriction 166 helps to maintain the stability of the entire deposition system during operation. The particle concentration in the aerosol is determined by the CNC operating at a standard flow rate. An on-off valve 165 can be used to positively stop flow through the CNC 160.

The dynamic adjustment of the deposition time parameter is based on the measured aerosol concentration from counter 160 and deposition flow rate signals from restriction 104 and pressure sensor 105. With proper calibration, a very high deposition count accuracy of achieved. For example, a deposition count accuracy of ±3% is achieved, which is the combination of flow and concentration measurement accuracies.

The volumetric flow rates of DMA sheath flow, input aerosol flow to the DMA in line 12, the monodisperse aerosol flow in lines 88 and 102, and excess flow in line 90 directly affect the sizing accuracy of the DMA. If a DMA is calibrated at a certain temperature and pressure, the DMA may not give an accurate sizing response if it is used in an environment that has a different ambient temperature and/or pressure. Temperature sensor 56 and pressure transducer 54 measure DMA temperature and pressure (ambient temperature and pressure, and air/gas temperature and pressure inside the DMA). The signals from the real-time measurement of temperature and pressure are sent back to the controller 151 for proper compensation to the flow controllers and other variable parameters to ensure the sizing accuracy of the DMA.

As shown in FIG. 4, the DMA is an instrument that classifies particles according to electric mobility of the particles. It can be described as a cylindrical condenser consisting of a metal rod concentrically located within a metal tube. Polydisperse aerosol and clean sheath air are introduced into the DMA and flow down the annulus between the center electrode and the outer tube as laminar streams. A high DC voltage is applied to the center electrode while the outer tube is grounded. The electric field between the two cylindrical electrodes cause charged particles in the aerosol to deflect across the streamlines to the exit slit near the bottom of the tubular electrode rod. The voltage needed to deflect particles to the output air stream is then related to the electric mobility of the particles. The relation between the particle diameter and the required center rod voltage can be obtained using such known equations. In practical use, the voltage is scanned to find the peak voltage corresponding to the maximum particle concentration in the monodisperse aerosol output stream. The voltage is then used to calculate the corresponding particle size.

All size particles other than the selected size from the DMA, including residue particles and multiplets of the PSL spheres, are removed by electrostatic separation by the DMA. If the atomizing PSL solution has one PSL peak, the DMA will output the PSL spheres at the peak size. If the PSL solution contains multiple PSL size peaks, the DMA will output the peak size PSLs closest to the size specified by the operator. For example, if four PSL sizes are to be deposited onto a wafer, four containers with solutions which each contain one specific PSL sphere size are provided. The four PSL sphere sizes can be mixed and use the DMA system to output one PSL sphere size at a time for deposition.

The DMA system using two DMAs covers the size ranges of 100 to 2000 nm. The two DMA systems offer the highest accuracy and resolution in its size range. The low detection limit of the smaller DMA can be extended to 3 nm.

Classified deposition particle size, that is, using a mono-size aerosol from the output of the DMA, is much preferred for PSL or process particles smaller than 1000 nm. After being neutralized to remove excess charges from atomization in neutralizer 46 the aerosol is received by the DMA and classified by the DMA either by direct classification, or size distribution scan and classification. In the size distribution scan and classification mode, the aerosol from the atomizer is first scanned to determine the aerosol size distribution and then classified for deposition. In this operation mode, only the PSL spheres at the peak size are deposited regardless of the broadness of the original distribution of the PSL spheres in the atomizing solution. The PSL size in this operation mode is referred as the Label Size, which is given by the PSL sphere manufacturer. For creating Absolute Contaminant Standards, this operation mode is most widely used when United States National Institute of Science and Technology (NIST) or NIST traceable PSL spheres are used for deposition.

The classification-only operation mode is often preferred by experienced users. In this mode, the particle size is referred as the DMA size based on the particle's electrical mobility. Since the DMA is calibrated using NIST standard PSL spheres, the DMA size is in good agreement with the standard PSL spheres. The DMA has a sizing accuracy of ±2% while PSL spheres from different vendors may have as much as 10% difference in size. The DMA size is, therefore, more accurate than most Label Sizes including some NIST traceable PSL spheres.

The classification-only mode is also referred as the process particle deposition mode since it is widely used for process particle deposition. In process particle deposition, the original particles in atomization solution normally have a broad size distribution. With the classification mode of the DMA, the output particles for deposition can be any size within the original distribution. In this operation mode, the deposition can be made very fast, for example, up to 30 depositions per hour.

The chamber 110 has provisions for both spot deposition and full deposition. The spot deposition is useful since it can deposit multiple spots of different sizes on a single wafer. Advantages of using multiple spots include reduction in inspection system calibration time and cost, increase in calibration accuracy, improvement in inspection system performance and ease of monitoring the contamination level of the Wafer.

Although the present invention has been described with reference to preferred embodiments, workers skilled in the art will recognize that changes may be made in form and detail without departing from the spirit and scope of the invention.

What is claimed is:

1. A deposition device for depositing solid particles onto a substrate surface in a deposition chamber, said solid particles being carried in a gas forming an aerosol, comprising an atomizer having an atomizing nozzle for discharging an atomized liquid forming liquid droplets containing solid particles, and an impaction plate spaced from the atomizing nozzle in the atomizer against which the droplets containing the solid particles are impacted, said impaction plate being positioned to remove droplets above a selected size prior to discharge of the droplets from the atomizer into a fluid stream, a source of dry gas to evaporate the droplets in the fluid stream, the fluid stream being connected to be received by the deposition chamber.

2. The device of claim 1, wherein the fluid stream is carried in a flow line, and a valve in the flow line for selectively directing the aerosol to a first line and to a second line, the first line having a differential mobility analyzer to obtain a selected size of particles as a discharge to the deposition chamber.

3. The device of claim 2, wherein the second line provides a discharge of the aerosol directly to the deposition chamber.

4. The device of claim 2, wherein the first line has a junction which divides the aerosol in the first line into two individual flows, the first line carrying a first flow to the differential mobility analyzer and carrying particles thereto for classification as to size of particles to an outlet of the differential mobility analyzer, and the second flow being carried in a sheath flow line having a filter therein for removing selected particles, and connected to the differential mobility analyzer and providing a sheath flow of gas to the differential mobility analyzer.

5. The device of claim 2, wherein the first line leading to the differential mobility analyzer has a charge neutralizer for reducing electrical charges from the aerosol.

6. The device of claim 2, wherein the atomizer is provided with a clean gas at an inlet, a junction for diverting a portion of the clean gas through a branch line, said branch line connecting to an outlet of the differential mobility analyzer, to mix with an output of the differential mobility analyzer in a preselected ratio.

7. The device of claim 6, wherein said branch line has a flow controller therein, said flow controller controlling the amount of clean gas intermixed with the output from the differential mobility analyzer.

8. A wafer deposition system for depositing solid particles onto a wafer in an enclosed deposition chamber, a source of a dry gas carrying solid particles forming an aerosol flow in a first line connected to said chamber, an atomizer forming liquid droplets containing the solid particles, a source of dry gas connected to the first line to evaporate the droplets to leave the dry gas/solid particle aerosol flow in the first line, said first line having a branch line leading to a vacuum pump, said branch line being joined to said first line adjacent the deposition chamber, and a valve to direct the flow in the first line to the vacuum pump in a first state, and in a second state to close the branch line to direct the aerosol to the deposition chamber.

9. The deposition system of claim 8, wherein the vacuum pump draws a flow through the branch line that is greater than the flow from the source of aerosol, both the first line and branch line being connected to the deposition chamber, such that the deposition chamber is connected to the pump and air is removed from the deposition chamber when the valve is in its first state.

10. The deposition system of claim 8, wherein said first line carrying the aerosol flow has a second branch line connected thereto, upstream of the deposition chamber, said second branch line being selectively connected to direct aerosol flow through a particle counter, to monitor the particles carried in the aerosol flow in the first line.

11. A wafer deposition system for depositing particles onto a wafer in an enclosed deposition chamber, a source of an aerosol carrying particles, a first line connecting said source of aerosol to said chamber, said first line having a branch line leading to a vacuum pump, said branch line being joined to said first line adjacent the deposition chamber, and a valve to direct the flow in the first line to the vacuum pump in a first state, and in a second state to close the branch line to direct the aerosol to the deposition chamber, the source of aerosol comprising an atomizer having a nozzle with an outlet, an impaction plate mounted in alignment with the nozzle outlet for removing large particles from the aerosol prior to discharge from the atomizer.

12. The deposition system of claim 8, wherein said vacuum pump generates a flow of gas greater than the volume of the flow of the aerosol carried in the first line, said deposition chamber being connected to the first line and to the branch line, such that the vacuum pump, when connected to the first line removes gas from the deposition chamber as well as from the first line.

13. The deposition system of claim 8, wherein said aerosol is generated from an aerosol generator that suspends the particles in droplets carried in a gas stream, said aerosol generator having an output line connected to the first line, the sources of dry gas forming the aerosol flow and evaporating the droplets to leave dry gas/solid particle aerosol flow flowing in the first line, and a differential mobility analyzer for classifying particles in the first line, said differential mobility analyzer permitting a selected size of particles in the aerosol flow to be directed from the first line to the deposition chamber.

14. The deposition system of claim 13, wherein said flow in said first line is divided into two flows, a first of the flows being provided to the differential mobility analyzer, and a second of said flows in a sheath flow line having a filter therein for removing particles and the sheath flow line being connected to provide a sheath gas flow in the differential mobility analyzer.

15. The deposition system of claim 14 and a pressure sensor and a temperature sensor in the line providing a sheath gas flow to the differential mobility analyzer for providing feedback signals for controlling the differential mobility analyzer.

16. The deposition system of claim 14, wherein said differential mobility analyzer comprises an elongated cylindrical tube having an outer wall, a centrally located elongated electrode in said outer wall, a voltage provided to said electrode, a flow of gas on an interior surface of the differential mobility analyzer comprising the sheath gas flow, and an opening in said electrode for receiving particles of a selected size dependent upon parameters for controlling the differential mobility analyzer, said particles being discharged to the deposition chamber.

17. The deposition system of claim 13, wherein there is a second differential mobility analyzer, the second differential mobility analyzer being configured to provide particles at a different size range from the first mentioned differential mobility analyzer, and valves for controlling the flow of sheath gas and particle carrying aerosol selectively to each of the differential mobility analyzers.

18. The deposition system of claim 10 and a source of a clean gas connected to said first line upstream of said particle counter, said clean gas mixing with the aerosol flow to provide a desired concentration of particles as determined by the particle counter.

19. The deposition system of claim 18, wherein said source of clean gas is selectively connected through a flow controller directly to the deposition chamber for providing a purging flow through the deposition chamber.

20. The deposition system of claim 18, wherein the first line has a flow measurement device installed therein for determining the flow of aerosol to the deposition chamber.

21. The deposition system of claim 10, wherein the first line leading to the deposition chamber has a third branch line there, said third branch line being connected to a vacuum source, an on-off valve in the third branch line for coupling the vacuum source to the first line at selected times, said vacuum source drawing aerosol into the first line and to the vacuum source when the valve is open to precharge the first line with aerosol to be discharged into the deposition chamber.

* * * * *